United States Patent
Borgmeier et al.

(10) Patent No.: US 7,271,279 B2
(45) Date of Patent: Sep. 18, 2007

(54) METHOD FOR THE PRODUCTION OF UNSATURATED NITRILES FROM ALKANES

(75) Inventors: Frieder Borgmeier, Mannheim (DE); Frank Rosowski, Mannheim (DE); Goetz-Peter Schindler, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 425 days.

(21) Appl. No.: 10/482,326

(22) PCT Filed: Jun. 25, 2002

(86) PCT No.: PCT/EP02/07024

§ 371 (c)(1),
(2), (4) Date: Dec. 29, 2003

(87) PCT Pub. No.: WO03/002520

PCT Pub. Date: Jan. 9, 2003

(65) Prior Publication Data
US 2004/0199000 A1    Oct. 7, 2004

(30) Foreign Application Priority Data

| Jun. 29, 2001 | (DE) | 101 31 297 |
| Mar. 13, 2002 | (DE) | 102 11 275 |
| Apr. 22, 2002 | (DE) | 102 17 844 |

(51) Int. Cl.
C07C 253/18 (2006.01)
C07C 255/08 (2006.01)

(52) U.S. Cl. ........................ 558/320; 558/466
(58) Field of Classification Search ........... 558/320, 558/466
See application file for complete search history.

(56) References Cited

U.S. PATENT DOCUMENTS 5,268,497 A    12/1993    Ramachandran

FOREIGN PATENT DOCUMENTS

| EP | 0 193 310 | 9/1986 |
| EP | 0 328 280 | 8/1989 |
| EP | 0 336 592 | 10/1989 |
| EP | 0 372 972 | 6/1990 |
| EP | 0 381 369 | 8/1990 |

*Primary Examiner*—Golam M. M. Shameem
*Assistant Examiner*—Ebenezer Sackey
(74) *Attorney, Agent, or Firm*—Oblon, Spivak, McClelland, Maier & Neustadt, P.C.

(57) ABSTRACT

The invention relates to a process for preparing unsaturated nitrites from the corresponding alkanes which comprises the steps:
  a) feeding an alkane into a dehydrogenation zone and catalytically dehydrogenating the alkane to the corresponding alkene to obtain a product gas stream A which comprises the alkene, unconverted alkane and possibly one or more further gas components selected from the group consisting of steam, hydrogen, carbon oxides, hydrocarbons having a lower boiling point than the alkane or the alkene (low-boilers), nitrogen and noble gases,
  b) at least partially removing further gas components from the product gas stream A to give a feed gas stream B which comprises the alkane and the alkene,
  c) feeding the feed gas stream B, ammonia, an oxygen-containing gas and, if desired, steam into an oxidation zone and catalytically ammoxidizing the alkene to the corresponding unsaturated nitrile to give a product gas stream C which comprises the unsaturated nitrile, ammoxidation by-products, unconverted alkane and alkene and possibly one or more further gas components selected from the group consisting of steam, oxygen, carbon oxides, ammonia, nitrogen and noble gases,
  d) optionally removing ammonia from the product gas stream C to give an ammonia-depleted product gas stream D,
  e) removing the unsaturated nitrile and ammoxidation by-products from the product gas stream C or D by absorption in an aqueous absorbent to give a gas stream E which comprises unconverted alkane and alkene and possibly one or more further gas components selected from the group consisting of oxygen, carbon oxides, ammonia, nitrogen and noble gases, and an aqueous stream which comprises the nitrile and the by-products, and recovery of the unsaturated nitrile from the aqueous stream,
  f) recycling the gas stream E into the dehydrogenation zone.

5 Claims, No Drawings

METHOD FOR THE PRODUCTION OF UNSATURATED NITRILES FROM ALKANES

The invention relates to a process for preparing unsaturated nitrites from alkanes.

It is known that unsaturated nitrites such as acrylonitrile and methacrylonitrile can be prepared from the corresponding alkenes, propene and isobutene respectively, by what is known as ammoxidation of the alkene using an ammonia/oxygen mixture in the presence of a suitable catalyst. The relevant alkenes may be prepared in a preceding dehydrogenation step from the corresponding alkanes.

For instance, ammoxidation of propene gives acrylonitrile and ammoxidation of isobutene gives methacrylonitrile. In general, a methyl-substituted olefin yields the corresponding $\alpha,\beta$-unsaturated nitrile while the methyl group is converted into a nitrile group.

EP-A 0 193 310 describes a process for preparing acrylonitrile from propane which comprises catalytically dehydrogenating propane to give propene, ammoxidizing propene to give acrylonitrile, removing acrylonitrile from the product gas stream of ammoxidation and recycling unconverted propane and propene into the catalytic dehydrogenation. After removing acrylonitrile from the product gas stream of the ammoxidation, the hydrogen formed in the dehydrogenation is selectively combusted using oxygen over an oxidation catalyst to give water, which leaves a hydrogen-depleted gas stream comprising unconverted propane, propene, carbon oxides and low-boiling hydrocarbons. After removal of a sub-stream and recovery of unconverted propane and propene therefrom, this gas stream is recycled into the dehydrogenation step.

A disadvantage of this process is that the hydrogen resulting from the dehydrogenation in the subsequent ammoxidation may lead to the formation of explosive gas mixtures. The by-products resulting from the dehydrogenation also restrict the onstream time of the ammoxidation catalyst and lead to widening of the ammoxidation by-product spectrum.

It is an object of the present invention to provide an improved process for preparing acrylonitrile from propane.

We have found that this object is achieved by a process for preparing unsaturated nitrites from the corresponding alkanes which comprises the steps:

a) feeding an alkane into a dehydrogenation zone and catalytically dehydrogenating the alkane to the corresponding alkene to obtain a product gas stream A which comprises the alkene, unconverted alkane and possibly one or more further gas components selected from the group consisting of steam, hydrogen, carbon oxides, hydrocarbons having a lower boiling point than the alkane or the alkene (low-boilers), nitrogen and noble gases, b) at least partially removing further gas components from the product gas stream A to give a feed gas stream B which comprises the alkane and the alkene, c) feeding the feed gas stream B, ammonia, an oxygen-containing gas and, if desired, steam into an oxidation zone and catalytically ammoxidizing the alkene to the corresponding unsaturated nitrile to give a product gas stream C which comprises the unsaturated nitrile, ammoxidation by-products, unconverted alkane and alkene and possibly one or more further gas components selected from the group consisting of steam, oxygen, carbon oxides, ammonia, nitrogen and noble gases, d) optionally removing ammonia from the product gas stream C to give an ammonia-depleted product gas stream D, e) removing the unsaturated nitrile and ammoxidation by-products from the product gas stream C or D by absorption in an aqueous absorbent to give a gas stream E which comprises unconverted alkane and alkene and possibly one or more further gas components selected from the group consisting of oxygen, carbon oxides, ammonia, nitrogen and noble gases, and an aqueous stream which comprises the unsaturated nitrile and the by-products, and recovery of the unsaturated nitrile from the aqueous stream, f) recycling the gas stream E into the dehydrogenation zone.

In a process step a), the alkane is fed into a dehydrogenation zone and catalytically dehydrogenated to give the corresponding alkene.

Alkane starting materials for the process according to the invention are generally $C_3$-$C_{14}$-alkanes, and preference is given to propane and isobutane. The latter may be obtained, for example, from LPG (liquefied petroleum gas) or LNG (liquefied natural gas).

Alkanes may be dehydrogenated to give alkenes by oxidative dehydrogenation.

Oxidative alkane dehydrogenation may be carried out, for example, over Mo/V mixed oxide catalysts as described in U.S. Pat. No. 4,250,346 or over NiO catalysts at temperatures of from 300 to 500° C. and alkane conversions of from 10 to 20% as described in WO 00/48971.

Preference is given to carrying out alkane dehydrogenation as a non-oxidative catalytic dehydrogenation. This involves partially dehydrogenating the alkane in a dehydrogenating reactor over a dehydrogenating catalyst to give the alkene. The dehydrogenation results, as well as hydrogen, in the formation of small quantities of low-boiling hydrocarbon as cracking product of the alkane which, in the case of propane dehydrogenation includes, for example, methane, ethane and ethene. Depending on the dehydrogenation method, carbon oxides ($CO$, $CO_2$), water and nitrogen may also be present in product gas mixture A of the alkane dehydrogenation. In addition, unconverted alkane is present in the product gas mixture.

The catalytic alkane dehydrogenation may be carried out with or without oxygen-containing gas as a co-feed.

Catalytic alkane dehydrogenation may in principle be carried out using all reactor types and methods known from the prior art. A comparatively comprehensive description of dehydrogenation processes used according to the invention is also contained in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A useful reactor type is the fixed bed tube reactor or tube bundle reactor. In these reactors, the catalyst (dehydrogenation catalyst and, where oxygen is used as co-feed, optionally a specialized oxidation catalyst) is disposed as a fixed bed in a reaction tube or in a bundle of reaction tubes. The reaction tubes are customarily indirectly heated by the combustion of a gas, for example a hydrocarbon such as methane, in the space surrounding the reaction tubes. It is favorable to apply this indirect form of heating only to about the first 20 to 30% of the length of the fixed bed and to heat the remaining bed length to the required reaction temperature by the radiant heat released in the course of indirect heating. Customary reaction tube internal diameters are from about 10 to 15 cm. A typical dehydrogenation tube bundle reactor comprises from about 300 to 1000 reaction tubes. The internal temperature in the reaction tubes is customarily in the range from 300 to 1200° C., preferably in the range from 600 to 1000° C. The working pressure is customarily from 0.5 to 8 bar, frequently from 1 to 2 bar, when a small steam dilution is used (similar to the Linde process for propane dehydrogenation), or else from 3 to 8 bar when a high steam dilution is used (similar to the steam active reforming process (STAR process) for dehydrogenating propane or butane of Phillips Petroleum Co., see U.S. Pat. No. 4,902,849, U.S. Pat. No. 4,996,387 and U.S. Pat. No. 5,389,342). Typical gas hourly space velocities (GHSV) are from 500 to 2000 $h^{-1}$, based on the alkane to be dehydrogenated. The catalyst shape may, for example, be spherical or cylindrical (hollow or solid).

Catalytic alkane dehydrogenation, as described in Chem. Eng. Sci. 1992 b, 47 (9-11) 2313, may also be carried out heterogeneously catalyzed in the fluidized bed without diluting the alkane. It is advantageous to operate two fluidized beds in parallel, of which one is generally in the process of regeneration. The operating pressure is typically from 1 to 2 bar, the dehydrogenation temperature generally from 550 to 600° C. The heat required for the dehydrogenation is introduced into the reaction system by preheating the dehydrogenation catalyst to the reaction temperature. When an oxygen-containing co-feed is admixed, it is possible to do without the preheater and to generate the required heat directly in the reactor system by combustion of hydrogen and/or of hydrocarbons in the presence of oxygen. If desired, a hydrogen-containing co-feed may additionally be admixed.

Catalytic alkane dehydrogenation may be carried out in a tray reactor. This comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by reaction gas. In general, such a tray reactor is operated using a fixed catalyst bed. In the simplest case, the fixed catalyst beds are disposed axially in a shaft furnace reactor or in the annular gaps of concentric cylindrical grids. A shaft furnace reactor corresponds to one tray. Carrying out the dehydrogenation in a single shaft furnace reactor corresponds to a preferred embodiment. In a further preferred embodiment, the dehydrogenation is carried out in a tray reactor having 3 catalyst beds. In a method which does not employ oxygen as a co-feed, the reaction gas mixture is subjected to intermediate heating in the tray reactor on its way from one catalyst bed to the next catalyst bed, for example, by passing it over heat exchanger plates heated by hot gases or by passing it through tubes heated by hot combustion gases.

In a preferred embodiment of the process according to the invention, the catalytic alkane dehydrogenation is carried out autothermally. To this end, the reaction gas mixture of the alkane dehydrogenation is additionally admixed with oxygen in at least one reaction zone and the hydrogen contained in the reaction gas mixture is combusted, which directly generates in the reaction gas mixture at least a portion of the heat required for dehydrogenation in the at least one reaction zone. A characteristic of the autothermal method compared to what could be termed an oxidative method is, for example, the presence of hydrogen in the effluent gas. The oxidative processes form no significant quantities of free hydrogen.

In general, the quantity of the oxygen-containing gas added to the reaction gas mixture is chosen in such a way that the heat quantity required for the dehydrogenation of the alkane is generated by the combustion of the hydrogen present in the reaction gas mixture and/or of the hydrocarbon present in the reaction gas mixture and/or of the hydrocarbons present in the form of coke. In general, the overall quantity of oxygen added, based on the total quantity of the alkane, is from 0.001 to 0.5 mol/mol, preferably from 0.005 to 0.2 mol/mol, more preferably from 0.05 to 0.2 mol/mol. Oxygen may either be added as pure oxygen or else as an oxygen-containing gas in a mixture with inert gases. Preference is given to using air as the oxygen-containing gas. The inert gases and the gases resulting from combustion generally provide additional dilution and therefore support the heterogeneously catalyzed dehydrogenation.

The hydrogen combusted to generate heat is the hydrogen formed by catalytic alkane dehydrogenation and also any hydrogen additionally added to the reaction gas mixture. The quantity of hydrogen should preferably be such that the $H_2/O_2$ molar ratio in the reaction gas mixture immediately after the oxygen is fed in is from 2 to 10 mol/mol. In multistage reactors, this applies to every intermediate oxygen feedpoint and any intermediate hydrogen feedpoint.

The hydrogen is combusted catalytically. The dehydrogenation catalyst used generally also catalyzes the combustion of the hydrocarbons and of hydrogen with oxygen so that in principle no additional specialized oxidation catalyst is necessary. In one embodiment, operation is effected in the presence of one or more oxidation catalysts which selectively catalyze the combustion of hydrogen to oxygen in the presence of hydrocarbons. The combustion of hydrocarbons with oxygen to give CO and $CO_2$ only occurs to a minor extent, which has a distinct positive effect on the selectivities achieved for the alkene formation. The dehydrogenation catalyst and the oxidation catalyst are preferably present in different reaction zones.

When the reaction is carried out in more than one step, the oxidation catalyst may be present in only one, in more than one or in all the reaction zones.

Preference is given to disposing the catalyst which selectively catalyzes the oxidation of hydrogen at the locations where there are higher oxygen partial pressures than at other locations in the reactor, in particular near the feedpoint for the oxygen-containing gas. The oxygen-containing gas and/or hydrogen may be fed in at one or more locations in the reactor.

In one embodiment of the process according to the invention, intermediate feeding in of oxygen-containing gas and of hydrogen occurs before every tray of a tray reactor. In a further embodiment of the process according to the invention, metering in of oxygen-containing gas and of hydrogen occurs before every tray except the first tray. In one embodiment, a layer of a specialized oxidation catalyst is present downstream of every feedpoint, followed by a layer of dehydrogenation catalyst. In a further embodiment, no specialized oxidation catalyst is present. The dehydrogenation temperature is generally from 400 to 1100° C., the pressure in the last catalyst bed of the tray reactor generally from 0.2 to 5 bar, preferably from 1 to 3 bar. The GHSV is generally from 500 to 2000 $h^{-1}$, and in high-load operation even up to 100 000 $h^{-1}$, preferably from 4000 to 16 000 $h^{-1}$, based on the alkane to be dehydrogenated.

A preferred catalyst which selectively catalyzes the combustion of hydrogen comprises oxides or phosphates selected from the group consisting of oxides or phosphates of germanium, tin, lead, arsenic, antimony, indium and bismuth. A further preferred catalyst which catalyzes the combustion of hydrogen comprises a noble metal of transition group VIII or I of the Periodic Table.

The dehydrogenation catalysts used generally have a support and an active composition. The support consists of a heat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof, as support. The mixtures may be physical mixtures or else chemical mixed phases such as magnesium aluminum oxide or zinc aluminum oxide mixed structures. Preferred supports include zirconium dioxide and/or silicon dioxide, and particular preference is given to mixtures of zirconium dioxide and silicon dioxide.

The active composition of the dehydrogenation catalysts generally comprises one or more elements of transition group VIII of the Periodic Table, preferably platinum and/or palladium, more preferably platinum. The dehydrogenation catalysts may further comprise one or more elements of main group I and/or II of the Periodic Table, preferably potassium and/or cesium. The dehydrogenation catalysts may further contain one or more elements of transition group III of the Periodic Table including the lanthanides and actinides, preferably lanthanum and/or cerium. Finally, the dehydrogenation catalysts may have one or more elements of main group III and/or IV of the Periodic Table, preferably one or more elements selected from the group consisting of boron, gallium, silicon, germanium, tin and lead, more preferably tin.

In a preferred embodiment, the dehydrogenation catalyst comprises at least one element of transition group VIII, at least one element of main group I and/or II, at least one element of main group III and/or IV and at least one element of transition group m including the lanthanides and actinides, of the Periodic Table.

For example, all dehydrogenation catalysts which are disclosed by WO 99/46039, U.S. Pat. No. 4,788,371, EP-A 705,136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107 may be used according to the invention. Particularly preferred catalysts for the above-described variants of autothermal alkane dehydrogenation include the catalysts according to Examples 1, 2, 3 and 4 of DE-A 199 37 107.

Preference is given to carrying out the alkane dehydrogenation in the presence of steam. The steam added serves as a heat carrier and supports the gasification of organic deposits on catalysts, which counteracts carbonization of the catalysts and increases the onstream time of the catalyst. The organic deposits are converted to carbon monoxide and carbon dioxide.

The dehydrogenation catalyst may be regenerated by methods known per se. For instance, steam can be added to the reaction gas mixture or, from time to time, an oxygen-containing gas may be passed over the catalyst bed at elevated temperature and the deposited carbon burnt off. The dehydrogenation catalyst may then be reduced in a hydrogen-containing atmosphere.

The alkane dehydrogenation may also be carried out by the circuit gas method described in the yet to be published German patent application P 102 11 275.4.

The alkane dehydrogenation gives a product gas mixture A which, as well as the alkene and unconverted alkane, comprises secondary components. Customary secondary components include hydrogen, water, nitrogen, CO and $CO_2$ and also hydrocarbons which have lower boiling points than the alkane and the alkene (low-boilers) which, in the case of propane dehydrogenation, include, for example, methane, ethane and ethene as cracking products. In the case of isobutane dehydrogenation, propane, propene, propine and allene may also be present as cracking products. The composition of the gas mixture leaving the dehydrogenation stage may be highly variable depending on the dehydrogenation method. For instance, when the preferred autothermal dehydrogenation with feeding in of oxygen and additional hydrogen is carried out, the product gas mixture A will have a comparatively high content of water and carbon oxides. Methods without feeding in of oxygen will provide a dehydrogenation product gas mixture A having a comparatively high hydrogen content. Customarily, it will be under a pressure of from 0.3 to 10 bar and frequently a temperature of 400 to 1200° C., in favorable cases from 450 to 800° C.

In a process step b), the further gas components other than the alkane and the alkene are at least partially, but preferably almost completely, removed from the product gas stream A.

The product gas stream leaving the dehydrogenation zone may be separated into two substreams, and only one of the two substreams may be subjected to the further process steps b) to f) as product gas stream A, while the second substream may be recycled directly into the dehydrogenation zone. However, preference is given to subjecting the entire dehydrogenation product gas stream to the further process steps b) to f) as product gas stream A.

In one embodiment of the process according to the invention, water is removed first. The water may be removed, for example, by condensing out by cooling and/or compressing the dehydrogenation product gas stream A and may be carried out in one or more cooling and/or compressing stages. Water removal is customarily carried out when the alkane dehydrogenation is carried out autothermally or is carried out isothermally with feeding in of steam (similarly to the Linde or STAR process for dehydrogenating propane) and consequently the product gas stream has a high water content.

The removal of the further gas components other than the alkane and alkene from the product gas stream may be carried out by customary separation processes such as distillation, rectification, membrane processes, absorption or adsorption.

The removal of the hydrogen contained in the product gas mixture A from the alkane dehydrogenation may be effected, optionally after cooling, for example in an indirect heat exchanger, may be passed through a membrane, generally in the form of a pipe, which is only permeable toward molecular hydrogen. If required, the removed molecular hydrogen may be at least partially used in the dehydrogenation or else be utilized in a different way, for example for generating electrical energy in fuel cells.

The carbon dioxide contained in the dehydrogenation product gas stream A may be removed by $CO_2$ gas scrubbing. The carbon dioxide gas scrubbing may precede a separate combustion stage in which carbon monoxide is selectively oxidized to give carbon dioxide.

In a preferred embodiment of the process according to the invention, the alkane and the alkene are removed from the noncondensable or low-boiling gas components such as hydrogen, carbon oxides, low-boiling hydrocarbons and, if present, nitrogen in an absorption/desorption cycle by means of a high-boiling absorbent to give a reaction gas stream b which essentially consists of the alkane and the alkene.

To this end, the product gas stream A, optionally after preceding water removal, is brought into contact with an inert absorbent in an absorption step and the alkane and the alkene are absorbed by the inert absorbent to give an absorbent loaded with the alkane and alkene and an offgas comprising the remaining gas components. In a desorption step, the alkane and the alkene are released from the absorbent.

Inert absorbents used in the absorption stage are generally high-boiling nonpolar solvents in which the alkane/alkene mixture to be removed has a distinctly higher solubility than the remaining components of the product gas mixture. The absorption may be effected by simply passing the dehydrogenation product gas mixture through the absorbent. It may also be effected in columns or in rotation absorbers. Operation may be effected in cocurrent, countercurrent or cross current. Examples of useful absorption columns include tray columns having bubble cap trays, centrifugal trays and/or sieve trays, columns having structured packings, for example, sheet metal packings having a specific surface area of from 100 to 1000 $m^2/m^3$ such as Mellapak® 250 Y, and columns having random packings. It is also possible to use trickle towers and spray towers, graphite block absorbers, surface absorbers such as thick film and thin film absorbers and rotary columns, plate scrubbers, cross-spray scrubbers and rotary scrubbers.

Useful absorbents include comparatively nonpolar organic solvents, for example aliphatic $C_8$- to $C_{18}$-alkenes, or aromatic hydrocarbons such as the middle oil fractions from paraffin distillation, or ethers having bulky groups, or mixtures of these solvents, and a polar solvent such as 1,2-dimethyl phthalate. Further useful absorbents include esters of benzoic acid and phthalic acid with straight-chain $C_1$-$C_8$-alkanols, such as n-butyl benzoate, methyl benzoate, ethyl benzoate, dimethyl phthalate, diethyl phthalate, and also what are known as heat carrier oils, such as biphenyl and diphenyl ether, chloro derivatives thereof and also triarylalkenes. A useful absorbent is a mixture of biphenyl and diphenyl ether, preferably in the azeotropic composition, for example the commercially obtainable Diphyl®. This solvent mixture frequently comprises dimethyl phthalate in a quantity of from 0.1 to 25% by weight. Useful absorbents also include octanes, nonanes, decanes, undecanes, dodecanes, tridecanes, tetradecanes, pentadecanes, hexadecanes, heptadecanes and octadecanes and fractions obtained from refinery streams which have the linear alkanes mentioned as the main components.

Desorption is carried out by heating the loaded absorbent and/or depressurizing it to a lower pressure. Alternatively, desorption may also be carried out by stripping or by a combination of depressurizing, heating and stripping in one or more process steps. The absorbent regenerated in the desorption stage is recycled into the absorption stage.

A feed gas stream B is obtained which comprises the alkane and the alkene and is substantially free of the further gas components.

In one process variant, the desorption step is carried out by depressurizing and/or heating the loaded absorbent. In this case, a feed gas stream B is obtained which essentially consists of the alkane and the alkene.

When the desorption is carried out according to a further process variant by (additional) stripping of the absorbent, the feed gas stream B comprises the stripping gas, as well as the alkane and the alkene. In an advantageous process variant, the stripping gas used is an oxygen-containing gas in the quantities required for the subsequent ammoxidation.

The removal b) is generally incomplete so that, depending on the method of removal, small quantities or else only traces of the further gas components (for example the low-boiling hydrocarbons) may still be present in the feed gas stream B.

The at least partial removal of the further gas components from the dehydrogenation product gas stream A before feeding the gas stream into the ammoxidation brings a series of advantages. For instance, the formation of explosive gas mixtures in the ammoxidation reactor by preceding removal of hydrogen formed by the dehydrogenation is avoided. The removal of the by-products resulting from the dehydrogenation, for example the low-boiling cracking products of the alkanes to be dehydrogenated, firstly has a positive effect in the subsequent catalytic ammoxidation on the stability of the catalyst, whose onstream time is increased. Secondly, by-product formation, for example the formation of acetaldehyde and acetic acid from ethylene, is suppressed.

In a process step c), the feed gas stream B comprising the alkane and the alkene, ammonia, oxygen-containing gas and, if desired, steam are fed into an oxidation zone and an ammoxidation of the alkene to the corresponding unsaturated nitrile is carried out.

The catalytic ammoxidation is carried out in a manner known per se. The ammoxidation is customarily carried out at temperatures of from 375 to 550° C. and pressures of from 0.1 to 10 bar at a molar ratio of ammonia to alkene of from 0.2:1 to 2:1. Useful catalysts are known to those skilled in the art and described, for example, in WO95/05241, EP-A 0 573 713, U.S. Pat. No. 5,258,543 and U.S. Pat. No. 5,212, 317. The ammoxidation may be carried out in a tube reactor which contains the catalyst in particulate form and is surrounded by a cooling liquid for dissipating the heat of reaction. Preference is given to carrying out the ammoxidation in a fluidized bed reactor. The volume ratio of oxygen to alkene is customarily from 1.6:1 to 2.4:1. The volume ratio of ammonia to alkene is customarily from 0.7:1 to 1.2:1.

The oxygen-containing gas which is fed into the oxidation zone may be pure oxygen, air or oxygen-enriched or oxygen-depleted air. The preferred oxygen-containing gas is air.

A product gas stream C is obtained which comprises the unsaturated nitrile, ammoxidation by-products and unconverted alkane and alkene, and may possibly comprise steam, oxygen, carbon oxides, ammonia, nitrogen and/or noble gases.

For example, the product gas stream C of ammoxidation of propene to give acrylonitrile may comprise ammoxidation by-products acrolein, acetonitrile and HCN. The product gas stream C of ammoxidation of isobutene to give methacrylonitrile may comprise ammoxidation by-products methacrolein, HCN, acetonitrile and acrylonitrile.

In general, but not necessarily, the ammoxidation product gas stream C also comprises oxygen, ammonia and frequently also carbon oxides. When operation is effected using air as the oxygen-containing gas, it comprises nitrogen and noble gases and, when operation is effected while feeding in steam, also comprises steam.

Optionally, ammonia may be removed from the product gas stream C in a process step d) to give a highly ammonia-depleted or an ammonia-free product gas stream D.

In one process variant, a separate ammonia removal d) is effected by bringing the hot ammoxidation product gas stream C into contact with aqueous sulfuric acid in a quenching tower and thus washing ammonia out of the product gas stream C as ammonium sulfate. This gives an aqueous ammonium sulfate solution which may comprise dissolved unsaturated nitrile and also ammoxidation by-products. These may be stripped out of the aqueous ammonium sulfate solution in a downstream vapor stripper using steam and fed to further distillative workup.

In a further process variant, no separate ammonia removal d) is effected. However, ammonia is substantially, if not completely, removed from the ammoxidation product gas stream in the subsequent absorption step e) by absorption in the aqueous absorbent.

Alternatively, ammonia may also be removed from the ammoxidation product gas mixture by feeding methanol, which reacts with ammonia to give HCN, water and carbon dioxide, into the upper portion of the fluidized bed reactor where the ammoxidation is carried out (from about 85 to 95% of the total length).

In one process step e), the unsaturated nitrile and any ammoxidation by-products are removed from the product gas stream C or D by absorption in an aqueous absorbent. To this end, the product gas stream C or D is brought into contact with the aqueous absorbent in a gas scrubber to give an aqueous stream comprising the unsaturated nitrile, any ammoxidation by-products and any ammonia, from which the unsaturated nitrile is subsequently recovered, and a gas stream E which comprises unconverted alkane and alkene and any oxygen, carbon oxides, ammonia, nitrogen and/or noble gases.

When the product gas stream from which the unsaturated nitrile is washed out by the aqueous absorbent still comprises significant ammonia quantities, because, for example, there was no ammonia removal d), ammonia will be at least partially dissolved in the aqueous absorbent by the formation of ammonium carbonate in the presence of carbon dioxide likewise present in the product gas stream.

The unsaturated nitrile is recovered from the aqueous stream obtained in the absorption stage by distillation. For example, in the case of acrylonitrile preparation from propane, the aqueous stream resulting from the absorption stage may be separated in a first distillation column into a top stream consisting of crude acrylonitrile and a bottom stream comprising acetonitrile, water and high-boilers. The crude acrylonitrile obtained as the top stream, which in particular also contains HCN, may be further purified by distillation. Pure acetonitrile may be recovered from the bottom stream by distillation. The workup in the case of methacrylonitrile preparation is similar.

Finally, the gas stream E, which comprises unconverted alkane and alkene and may comprise oxygen, carbon oxides, ammonia, nitrogen and/or noble gases, is recycled into the dehydrogenation zone (step a)). The presence of ammonia in the recycled gas stream E is not disadvantageous for the alkane dehydrogenation. This is oxidized in the autothermal dehydrogenation method to give nitrogen or nitrogen oxides.

The presence of (residual) oxygen in the recycled gas stream E reduces the thermodynamic limitation of the alkane dehydrogenation, since the residual oxygen reacts with the hydrogen formed in the dehydrogenation and the equilibrium is thus shifted toward the product side. Since the dehydrogenation results in the volume increase, dilution by gases in the gas stream E likewise has a positive effect on the equilibrium point.

We claim:

1. A process for preparing unsaturated nitriles from the corresponding alkanes which comprises the steps:
    a) feeding an alkane and oxygen or an oxygen-containing gas into a dehydrogenation zone and catalytically dehydrogenating the alkane to the corresponding alkene to obtain a product gas stream A which comprises the alkene, unconverted alkane and one or more further gas components selected from the group consisting of steam, hydrogen, carbon oxides, hydrocarbons having a lower boiling point than the alkane or the alkene (low-boilers), nitrogen and noble gases, wherein the dehydrogenation is carried out autothermally,
    b) at least partially removing further gas components from the product gas stream A to give a feed gas stream B which consists essentially of the alkane and the alkene, by a process comprising contacting the product gas stream A with an inert absorbent in an absorption stage wherein the alkane and the alkene are absorbed by the inert absorbent to give an absorbent laden with the alkane and alkene and an offgas stream comprising the remaining gas components, and releasing the alkane and the alkene from the absorbent in a desorption stage,
    c) feeding the feed gas stream B, ammonia, an oxygen-containing gas and, if desired, steam into an oxidation zone and catalytically ammoxidizing the alkene to the corresponding unsaturated nitrile to give a product gas stream C which comprises the unsaturated nitrile, ammoxidation by-products, unconverted alkane and alkene and possibly one or more further gas components selected from the group consisting of steam, oxygen, carbon oxides, ammonia, nitrogen and noble gases,
    d) optionally removing ammonia from the product gas stream C to give an ammonia-depleted product gas stream D,
    e) removing the unsaturated nitrile and ammoxidation by-products from the product gas stream C or D by absorption in an aqueous absorbent to give a gas stream E which comprises unconverted alkane and alkene and possibly one or more further gas components selected from the group consisting of oxygen, carbon oxides, ammonia, nitrogen and noble gases, and an aqueous stream which comprises the nitrile and the by-products, and recovery of the unsaturated nitrile from the aqueous stream,
    f) recycling the gas stream E directly into the dehydrogenation zone.

2. A process as claimed in claim 1, wherein the absorption stage is preceded by a water removal operation.

3. A process as claimed in claim 1, wherein, in step d), ammonia is removed as ammonium sulfate by scrubbing with sulfuric acid.

4. A process as claimed in claim 1, wherein the alkane is propane, the alkene is propene and the unsaturated nitrile is acrylonitrile.

5. A process as claimed in claim 1, wherein the alkane is isobutane, the alkene is isobutene and the unsaturated nitrile is methacrylonitrile.

* * * * *